United States Patent [19]

Kelman

[11] Patent Number: 5,074,876
[45] Date of Patent: Dec. 24, 1991

[54] TWO PIECE INTRAOCULAR LENS

[76] Inventor: Charles D. Kelman, 269 Grand Central Pkwy., Floral Park, N.Y. 11005

[21] Appl. No.: 128,730

[22] Filed: Dec. 4, 1987

[51] Int. Cl.$^5$ .............................................. A61F 2/16
[52] U.S. Cl. ............................................................ 623/6
[58] Field of Search ........................................ 623/6, 6

[56] References Cited

U.S. PATENT DOCUMENTS

| 4,596,578 | 6/1986 | Kelman | 623/6 |
| 4,605,409 | 8/1986 | Kelman | 623/6 |
| 4,608,049 | 8/1986 | Kelman | 623/6 |
| 4,678,469 | 7/1987 | Kelman | 623/6 |
| 4,704,124 | 11/1987 | Shearing | 623/6 |

Primary Examiner—Randall L. Green
Assistant Examiner—David H. Willse
Attorney, Agent, or Firm—Darby & Darby

[57] ABSTRACT

Two piece intraocular lens for successive insertion of the two pieces through a minimum size incision into the eye for assembly therein to form the two piece lens for implantation in the eye, including an oblong lens body and a separate ring shaped collapsible tension frame therefor containing light-masking material for inhibiting light rays directed toward the outer edge portions of the lens body from being scattered thereby toware the retina after the assembly two pieces lens has been implanted in the eye.

17 Claims, 2 Drawing Sheets

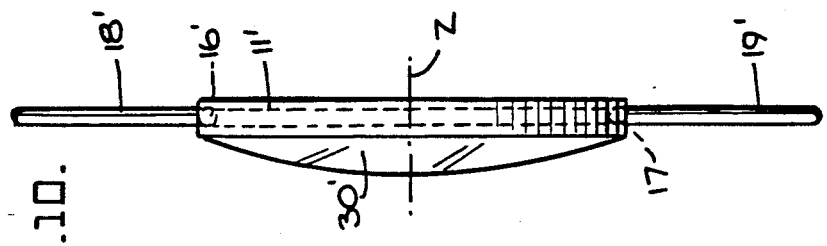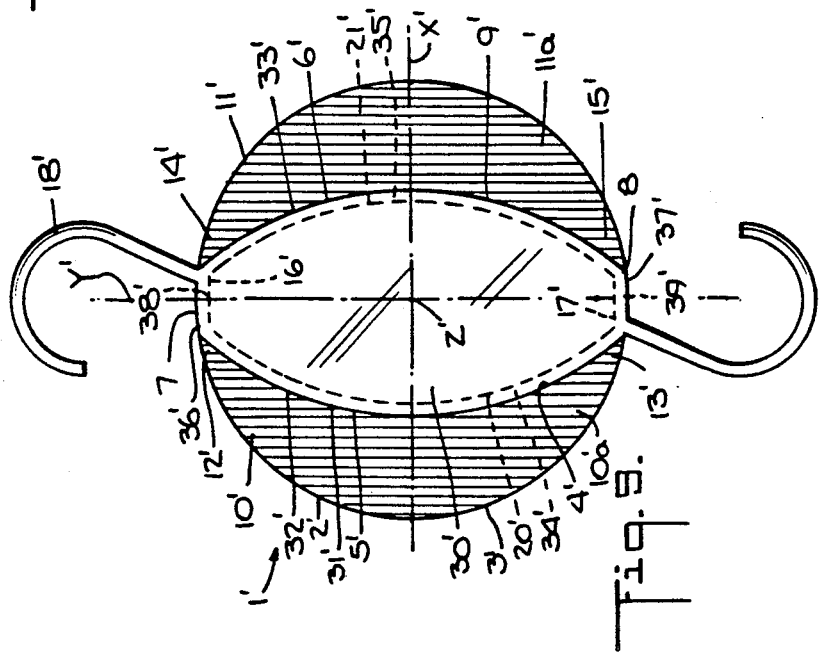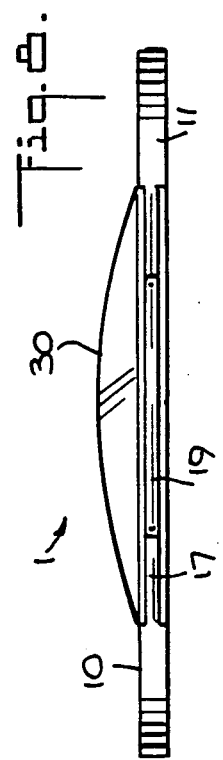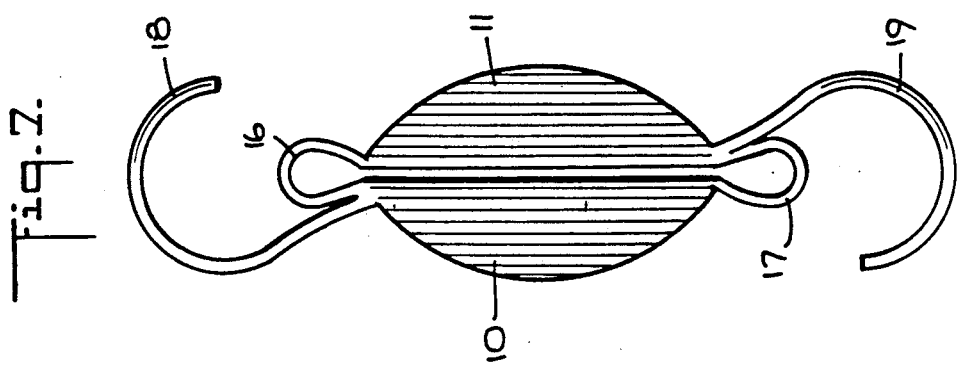

TWO PIECE INTRAOCULAR LENS

FIELD AND BACKGROUND OF THE INVENTION

The present invention relates to a two piece intraocular lens, and more particularly to an artificial intraocular lens for implantation in an eye, such as in the posterior chamber, after extracapsular removal of the natural eye lens, wherein the two pieces are independently successively inserted through a minimum size incision into the eye for assembly therein to form the two piece lens, and include an oblong lens body or optic and a separate ring shaped collapsible tension frame therefor which contains light masking means for inhibiting light rays directed toward the outer edge portions of the lens body from being scattered thereby toward the retina after the assembled lens has been implanted in the eye.

For treatment of conditions such as natural eye lens cataracts, a known eye surgery procedure is to remove the cataracted lens through a minimum size incision in the wall of the cornea of the eyeball, and replace it by an artificial intraocular lens as an internal implant lens. One specific surgical procedure involves the extracapsular removal of the natural eye lens, leaving portions of the posterior lens capsule intact to serve as a positioning site for the intraocular lens to be implanted in the eye.

U.S. Pat. No. 4,605,409 to Kelman discloses a one piece intraocular lens of the above type, having a small size lens body or optic, flexible position fixation haptics, and deformable masking means, such as laterally disposed flat planar wings temporarily contracted to provide the lens with a reduced girth permitting insertion through such a minimum size corneal incision into an eye. Upon implantation, the wings mask the optic side edge portions to overcome the edge glare effect of otherwise scattered incoming light rays at the peripheral marginal regions of the small size lens, such light masking being achieved by leaving the wing surfaces in rough, unground, condition, or by providing an opaque coating thereon.

U.S. Pat. No. 4,056,855 to Kelman shows a two piece intraocular lens, including an elliptically shaped lens member formed of a central lens body or optic and end tongues, and a separate similarly shaped non-collapsible, continuous closed loop wire frame resiliently self-clampable only to the lens body, once the two pieces are independently inserted through a minimum size corneal incision into an eye for like implantation purposes. The frame ends are arranged in the posterior chamber behind the iris and the lens member end tongues are arranged in the anterior chamber in front of the iris, both serving as position fixation means, while the optic is situated across the pupil. No light masking means of the above type are present.

U.S. Pat. No. 4,596,578 to Kelman shows a two piece intraocular lens, including an oblong rectangularly shaped lens body or optic and a separate frame having a similarly shaped noncollapsible split ring formed of cantilever flexible arms for embracingly receiving the optic and also serving as light masking means, and cantilever end limbs as position fixation means, the two pieces being independently inserted through a minimum size incision into the eye for assembly therein. The split ring is needed to permit the flexible arms to be separated for snaking the resulting open ring conformation through the incision and thereafter for enclosing the flexible arms around the optic to assemble the lens prior to implantation.

It would be desirable to provide a minimum size intraocular lens for implantation in an eye, following extracapsular removal of the natural eye lens, permitting rapid and efficient lens insertion through the same minimum size corneal incision used to remove the natural lens, and at the same time provide light masking means for the lens body, while utilizing a structurally simple arrangement of parts, readily fabricated at relatively low cost from widely available materials.

SUMMARY OF THE INVENTION

It is among the objects and advantages of this invention to overcome the drawbacks and deficiencies of the prior art, and to provide a two piece artificial intraocular lens for successive insertion of the two separate pieces through a minimum size incision into an eye for assembly in situ therein to form the two piece lens for implantation, e.g. after extracapsular removal of the natural eye lens, the two piece lens including a minimum width oblong lens body or optic and a separate ring shaped collapsible tension frame for the optic, having light masking means for inhibiting light rays directed toward the outer edge of the optic from being scattered thereby toward the retina after lens implantation.

It is among the additional objects and advantages of this invention to provide a two piece intraocular lens of the foregoing type, of minimum insertion width individual pieces permitting maximum accommodation of a small size optic through a minimum size eye incision, plus a frame therefor that does not require a larger incision than that needed for the optic, and which can be rapidly and efficiently inserted into the eye, assembled therein and then implanted, and still provide light masking for the optic.

It is among the further objects and advantages of this invention to provide such a two piece intraocular lens, which is readily fabricated at relatively low cost from widely available materials of desired characteristics, and which utilizes a structurally simple arrangement of cooperating parts.

According to this invention, a two piece artificial intraocular lens is provided for successive independent insertion of the two pieces through a minimum size incision into the eye for assembly therein to form the two piece lens for implantation in the eye, e.g. following extracapsular removal of the natural eye lens.

The two piece intraocular lens comprises an oblong lens body or optic, having an outer edge defining two opposed longer sides and two opposed shorter sides, and a separate continuous and uninterrupted ring shaped collapsible tension frame, having a generally circular outer edge and an inner edge defining two opposed longer sides and two opposed shorter sides, and forming an oblong aperture sized and shaped for receiving and peripherally embracing the lens body or optic under tension.

The frame includes two opposed longer side oblong planar wing members defining light masking means and having generally pointed ends, and two opposed shorter side collapsibly deformable linear tension filaments interconnecting correspondingly adjacent ends of the wing members to form the continuous and uninterrupted ring shaped collapsible tension frame, preferably with one or both of the filaments being locally flexible and/or slightly resiliently stretchable.

Advantageously, the shorter sides of the lens body outer edge are provided with grooves for receiving the filaments correspondingly therein, and the longer sides of the lens body outer edge and the adjacent wing member edge portions are optionally provided with coacting seating formations for retaining the lens body against displacement in a direction crosswise of the plane of the corresponding wing member. In particular, the formations may include grooves in the lens body and groove engaging extensions on the corresponding wing member edge portions.

Position fixation means, such as a haptic connected to each wing member, are favorably provided on the frame for seating the lens in the eye. Also, the wing member light masking means may comprise optically opaque means or optically translucent means.

Preferably, the lens body has a maximum dimension in the oblong width direction thereof of about 3 mm, and the wing members each have a maximum dimension in the oblong width direction thereof of about 1.5 mm. The lens body and wing members are conveniently made of shape retaining plastic and the filaments of locally flexible and slightly resiliently stretchable plastic.

In one preferred form, the lens body has a generally rectangular oblong shape and the wing members each have the shape of a segment of a circle whose chord is defined by a corresponding longer side of the inner edge forming the aperture. In another preferred form, the lens body has a generally elliptical oblong shape and the wing members each have the shape of a convexo-concave crescent, with a convex side defined by a portion of the circular outer edge of the frame, and a concave side defined by a corresponding longer side of the inner edge forming the aperture.

BRIEF DESCRIPTION OF THE DRAWINGS

Other and further objects and advantages of the present invention will become apparent from the within specification and accompanying drawings, in which:

FIG. 7 is a plan view showing the wing members of the frame of FIG. 1 drawn into abutment with each other to form another minimum size collapsed condition insertable compact unit analogous to that shown in FIG. 6;

FIG. 8 is a schematic bottom end view of the two piece lens in assembled form as it would exist in the eye prior to implantation;

FIG. 9 is a plan view of the front or anterior side of the lens body assembled with the continuous and uninterrupted ring shaped collapsible tension frame, including light-masking wing members containing haptics thereon, to form a two piece artificial intraocular lens according to a generally elliptically shaped oblong lens body embodiment of the present invention; and FIG. 10 is a right lateral side view of FIG. 9.

DESCRIPTION OF THE PREFERRED EMBODIMENTS

Figure 1:
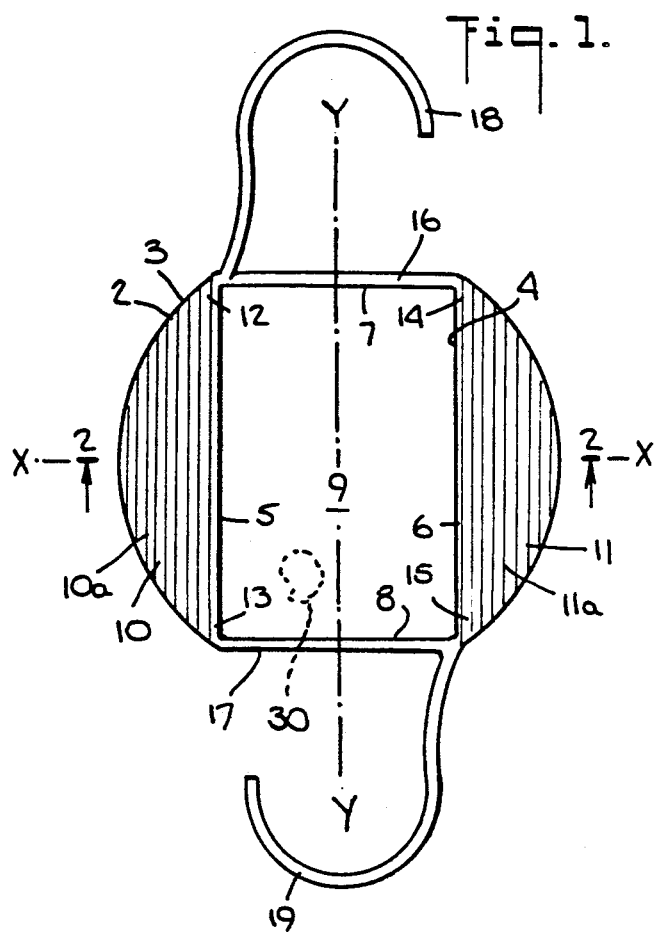
FIG. 1 is a plan view of the front or anterior side of the continuous and uninterrupted ring shaped collapsible tension frame, including light-masking wing members containing haptics thereon, forming one piece of the two piece artificial intraocular lens according to a generally rectangularly shaped oblong lens body embodiment of the present invention.
Figure 3:
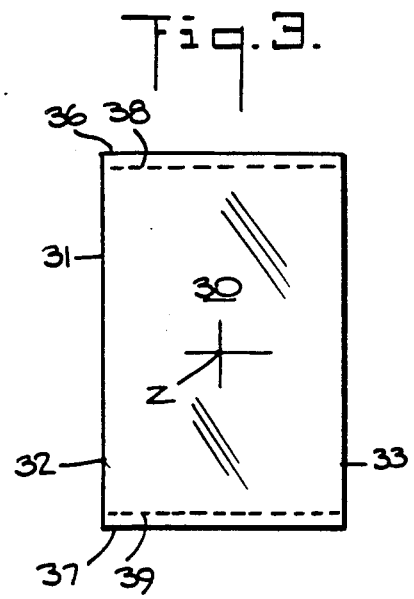
FIG. 3, 4 and 5 are front or anterior side plan, bottom end, and left lateral side, views, respectively, of the lens body or optic forming the other separate piece of the two piece artificial intraocular lens used with the frame of FIG. 1 to provide the two piece lens according to said embodiment.
Figure 2:
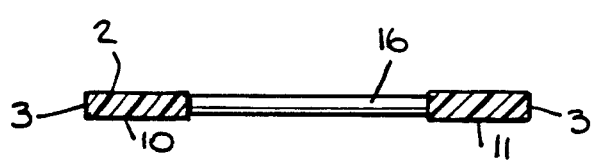
FIG. 2 is a sectional view taken along line 2—2 of FIG. 1.
Figure 4:
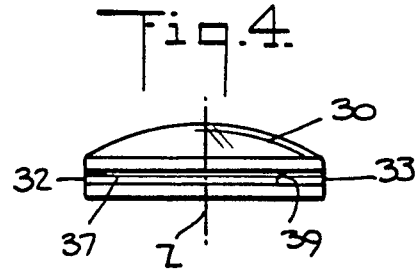
Figure 5:
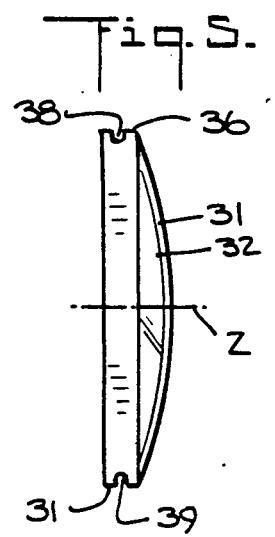

Referring to the drawings, and initially to FIGS. 1-2, a separate continuous and uninterrupted ring shaped collapsible tension frame 2 is shown, constituting one piece of a two piece artificial intraocular lens 1 (FIG. 8), according to one embodiment of the present invention, in which the other piece is an oblong lens body or optic 30 of generally rectangular shape (FIG. 3-5).

Frame 2 has a generally circular outer edge 3, and an inner edge 4 defining two opposed longer sides 5,6 and two opposed shorter sides 7,8, and forming an oblong central aperture 9 of generally rectangular shape, specifically sized and shaped for receiving and peripherally embracing optic 30 (shown schematically in phantom in FIG. 1) under tension.

Frame 2 includes two opposed longer side oblong planar wing members or wings 10,11, which define light masking means 10a,11a, such as by providing wings 10,11 as opaque members or translucent members, or by providing such members with opaque or translucent surfaces. Oblong wings 10,11 have generally pointed ends 12,13 and 14,15, respectively. Frame 2 further includes two opposed shorter side collapsibly deformable linear tension filaments 16,17, which interconnect adjacent ends 12 and 14, and 13 and 15, of wings 10 and 11, as shown.

The interconnection of filaments 16 and 17 with such ends of wings 10 and 11 thereby forms the continuous and uninterrupted structure of the ring shaped collapsible tension frame 2. Necessarily, the dimensions of aperture 9 and optic 30, and especially the length of filaments 16,17, will be precisely selected and conformed with each other to assure that optic 30 will be snapped into aperture 9 and held in place in frame 2 under slight tension, as described below. At the same time filaments 16,17 will necessarily be more or less self-collapsibly deformable to assure the temporary collapse of frame 2 for insertion through the minimum size corneal incision.

It will be noted that, although frame 2 may be effectively seated via wings 10,11 as position fixation means in the eye, e.g. in the posterior chamber remaining after extracapsular removal of the natural eye lens by the surgeon, preferably frame 2 is provided with opposed haptics 18,19 as particular, e.g. limitedly flexible, position fixation means, in the usual manner. For this purpose, haptic 18 is connected to end 12 of wing 10, and haptic 19 is connected to the diagonally opposite end 15 of wing 11.

The connections between wings 10,11 and filaments 16,17, and those between haptics 18,19 and wing ends 12,15, as the case may be, are preferably integral connections.

The oblong generally rectangularly shaped lens body or optic 30, as shown in FIGS. 3-5, has an outer boundary edge 31 which defines two opposed longer sides 32,33, and two opposed shorter sides 36,37, the latter being respectively provided with grooves 38,39. Optic 30 has a selective curvature profile for providing the desired optical refractive characteristics for the lens, in known manner.

In accordance with one well known surgical procedure, for example, the surgeon will remove the natural lens and a portion of the anterior wall part of the natural lens capsule via the usual small size corneal incision, e.g. 3 mm, leaving intact the posterior wall part of the lens capsule, which is held in place by the zonules or suspensory ligament and fibers attached to its external periphery. The internal periphery of the posterior wall part forms a recessed anterior cul-de-sac or ciliary sulcus which efficiently serves as a posterior chamber seating location for the haptics of the two piece intraocular lens.

As may be appreciated from a comparison of FIGS. 1, 3 and 8, optic 30 and central aperture 9 of frame 2 are of complemental conforming size and shape. Thus, after successive insertion of these two pieces through the corneal incision into the eye, optic 30 may be placed in aperture 9, with optic shorter groove 38 aligned with frame filament 16, optic longer sides 32,33 aligned with wings 10,11 at frame longer sides 5,6, and optic shorter groove 39 aligned with frame filament 17, e.g. such that optic shorter groove 39 is preliminarily seated onto frame filament 17 as a fulcrum or hinge, and slight pressure applied by the surgeon to snap optic 30 into engagement with frame 2, to form the assembled two piece intraocular lens in situ in the eye.

Preferably, one of the haptics 18,19 will first be positioned in the usual way in its desired location, e.g. in the posterior chamber, to stabilize frame 2, then optic 30 will be placed in juxtaposition with frame 2 and snapped into place in aperture 9, and thereafter the other of the haptics 18,19 will be positioned in its desired location, e.g. also in the posterior chamber, whereby to complete the lens implantation.

Of course, it will be understood that besides the nesting coation provided by optic grooves 38,39 and filaments 16,17, any suitable form of coacting seating formations may be used as retention seating means for retaining optic 30 against displacement in a direction crosswise of the plane of the corresponding wings 10,11, as the case may be, i.e. once optic 30 has been snapped in place in aperture 9. Such coacting retention seating means is required to assure positive resilient interconnection of these parts for effective "snapped in" seating disposition in desired spatial relation of optic 30 in aperture 9 under positive reserve tension in frame 2, utilizing the slightly resiliently stretchable nature of at least one of filaments 16,17 for this purpose.

The two piece construction of lens 1 facilitates exploitation of the minimum size corneal incision used by the surgeon for extracapsular removal of the natural eye lens, since each of the two pieces 2 and 30 may be separately successively independently inserted through that same minimum size incision into the eye for assembly therein. This is particularly significant since, understandably, the smaller the size of the corneal incision the less the trauma experienced by the patient, and in turn the less the pain and discomfort endured then and thereafter, not only because of the incision itself but also because of the number and/or size of any needed sutures.

Figure 6:
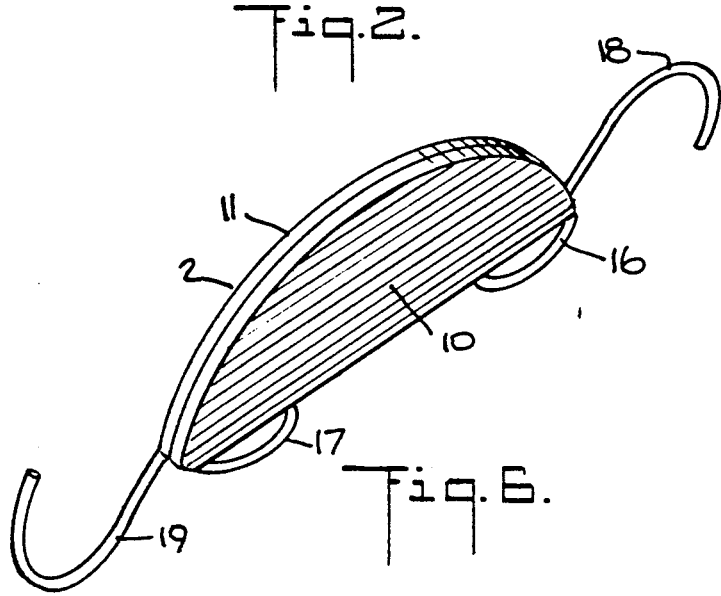
FIG. 6 is a perspective view of the frame of FIG. 1 folded onto itself to form a minimum size collapsed condition insertable compact unit.

Thus, because filaments 16,17 are made of self-collapsible deformable material, wings 10,11 may be simply folded onto each other as shown in FIG. 6, or drawn in side by side abutting relation, e.g. in the same plane, as shown in FIG. 7, or the like, each such appropriate form representing a minimum girth compact unit readily longitudinally insertable through that same minimum size incision. By providing optic 30 with an oblong shape, its width may be conformed to the size of that same incision whereby to provide a likewise minimum girth compact unit, as shown in FIG. 4, readily longitudinally insertable through such incision, after which the two pieces may be assembled into lens 1 as shown in FIG. 8.

The self-collapsibly deformable nature of frame 2 is effectively enhanced by providing one or both of filaments 16,17 of locally flexible material, and preferably of slightly resiliently stretchable material, as aforesaid, so as to assure the desired tension embracing of optic 30 by frame 2. Both of these contemplated characteristics are achieved by making filaments 16,17 of minimum cross sectional thickness, and using polymethylmethacrylate (PMMA) or Prolene, e.g. polypropylene synthetic textile fiber, or similar material, as the plastic material for filaments 16,17, while precisely determining the length of filaments 16,17 to assure that optic 30 will be held in frame 2 under slight resilient tension.

On the other hand, wings 10,11, as well as haptics 18,19, are conveniently provided of suitable shape retaining, yet optionally limitedly resilient or flexible, plastic material such as polymethylmethacrylate (PMMA), although they may also be made of polypropylene or silicone plastic should enhanced deformable characteristics for these parts be especially desired. Optic 30 is preferably made of rigid polymethylmethacrylate (PMMA) so that it may be readily "snapped" into position, as aforesaid.

Of course, the optic will be formed of suitable light focusing material having the desired optical characteristics, and all materials used for the two piece lens must be compatible with the eye fluid environment in the interior of the eyeball, and thus be non-toxic. After the two pieces are inserted, assembled and implanted by the surgeon, they will advantageously retain their desired optical and other characteristics.

Favorably, optic 30 has a maximum dimension in the oblong width direction thereof of about 3 mm, and wings 10,11 each have a maximum dimension in the oblong width direction thereof of about 1.5 mm. These dimensions are readily accommodated in a minimum size corneal incision of for instance about 3 mm.

Thus, as may be appreciated from FIGS. 1 and 3, circular outer edge 3 of frame 2 preferably has a diameter of about 6 mm, which is generally considered the proper average size for an intraocular lens, and wings 10,11 have a maximum width at their widest crest portions of about 1.5 mm, so as to provide central aperture 9 with an oblong shorter side width of about 3 mm, i.e. along the horizontal axis X, and an oblong longer side length of about 5.5 mm, i.e. along the vertical axis Y, with filaments 16,17 representing truncated ends located at a maximum distance of about 0.25 mm each from the extension of the circle of circular outer edge 3 thereat (shown in phantom in FIG. 1).

In turn, optic 30 will have the same dimensions as aperture 9, i.e. an oblong shorter side width of about 3 mm and an oblong longer side length of about 5.5 mm, thereby assuring the tension held disposition of optic 30 in frame 2. The height or thickness of optic 30, i.e. along transverse optical axis Z (FIGS. 4–5), will depend on the selected optical characteristics of optic 30. Nevertheless, as may be seen from FIGS. 2, 4, 5 and 8, wings 10,11 are generally of thin, flat profile in cross section as compared to the thickened conventional size rounded curvature profile cross section of optic 30, e.g. with such optic having a maximum thickness dimension of about 1.5 mm.

In terms of the geometrical shape of the generally oblong rectangular embodiment per frame 2, it will be seen that wings 10,11 form opposed longitudinal edges of frame 2, or more precisely of central aperture 9, which constitute segments of the circle bounded by circular outer edge 3, such that the elongated edges represented by longer sides 5,6 define chords of that circle. Also, the arrangement of the various parts of frame 2 and optic 30 is such that a diametrically symmetrical configuration is desirably provided, including preferably the diametrically opposed symmetrical disposition of haptics 18,19 on frame 2 with their curves extending in opposite directions.

FIGS. 9–10 show an alternative embodiment of a two piece intraocular lens 1' in which prime (') designations are assigned to analogous parts to those shown in FIGS. 1–8, here used to illustrate an oblong elliptically shaped lens body or optic 30' and a self-collapsibly deformable frame 2' having an oblong elliptically shaped central aperture 9', bounded on longer sides 5',6' by wing members 10',11' each having the shape of a convexo-concave crescent, with a convex outer side defined by a portion of circular outer edge 3', and a concave inner side defined by a corresponding longer side 5',6 ' of inner edge 4' forming aperture 9'.

In this case, self-collapsible filaments 16',17' are shorter due to the geometrical elliptically shaped construction involved and the arcuate nature of shorter sides 7',8' between the wing ends 12',14' and 13',15', respectively, whereas the oblong width and oblong length dimensions of the various parts, i.e. in terms of horizontal axis X' and vertical axis Y', are generally the same as in the rectangularly shaped construction of FIGS. 1–8. In any case, the construction of lens 1' of FIGS. 9–10 is such that optic 30' will readily snap into position in aperture 9' of frame 2' and be held under slight resilient tension therein in the same way as described above as regards the corresponding parts of lens 1 of FIGS. 1–8.

In particular, FIG. 9 indicates schematically the additional presence on wings 10',11' of optional extensions 20',21 ' projecting slightly into oblong elliptical central aperture 9' from inner edge 4', for positive seating coaction with corresponding optional longer grooves 34',35' in outer boundary edge 31' on longer sides 32',33' of optic 30'. These wing extensions 20',21' and optic longer grooves 34',35' serve as optional secondary coacting seating formations, in conjunction with frame filaments 16',17' and optic shorter grooves 38',39' which serve as primary coacting seating means, for retaining optic 30' against displacement in a direction crosswise of the plane of the corresponding wings 10',11', once optic 30' has been snapped in place in aperture 9'.

It is clear from the foregoing that the two piece lens assembly of each embodiment of the present invention constitutes a structurally simple arrangement of cooperating parts forming a construction which is readily fabricated at relatively low cost from widely available materials of desired characteristics.

It will be understood that the surgical procedures contemplated herein are well known to those skilled in the art, and that the nature and significance of the masking means as they relate to the small size optics used herein are the same as described more fully in the aforesaid U.S. Pat. Nos. 4,605,409 and 4,596,578.

By reason of the simple two piece construction involved, should it be found desirable or necessary at some future time, a new corneal incision can be made, the optic conveniently snapped out of the frame and removed from the eye through the new incision while the frame remains in place, and another optic, perhaps of different refractive characteristics, inserted in its place and snapped into the original frame as is, or after temporarily extracting one of the haptics from its posterior chamber position to facilitate reassembly before returning the haptic to its original position.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Two piece intraocular lens for successive insertion of the two pieces through a minimum size incision into the eye for assembly therein to form the two piece lens for implantation in the eye, which comprises:

an oblong lens body having an outer edge defining two opposed longer sides and two opposed shorted sides, and a separate continuous and uninterrupted ring shaped collapsible frame having a generally circular outer edge and an inner edge defining two opposed longer sides and two opposed shorter sides and forming an oblong aperture sized and shaped for receiving and peripherally embracing the lens body, the frame including two opposed longer side oblong planar wing members defining light-masking means and two opposed shorter side collapsibly deformable linear filaments interconnecting correspondingly adjacent ends of the wing members to form said continuous and uninterrupted ring shaped collapsible frame, at least one of said filaments being a linear tension filament made of locally flexible and slightly resiliently stretchable plastic for tensioning said frame to peripherally embrace the lens body under positive reserve tension.

2. Lens of claim 1 wherein the shorter sides of the outer edge of the lens body are provided with grooves for receiving the filaments correspondingly therein.

3. Lens of claim 1 wherein the longer sides of the outer edge of the lens body and the adjacent wing member edge portions are provided with coacting seating formations for retaining the lens body against displacement in a direction crosswise of the plane of the corresponding wing member.

4. Lens of claim 3 wherein the formations include grooves in the lens body and groove engaging extensions on the corresponding wing member edge portions.

5. Lens of claim 1 wherein position fixation means are provided on the frame for seating the lens in the eye.

6. Lens of claim 1 wherein the position fixation means include a haptic connected to each wing member.

7. Lens of claim 1 wherein the wing member light-masking means comprise optically opaque means.

8. Lens of claim 1 wherein the wing member light-masking means comprise optically translucent means.

9. Lens of claim 1 wherein the lens body has a maximum dimension in the oblong width direction thereof of about 3 mm, and the wing members each have a maximum dimension in the oblong width direction thereof of about 1.5 mm.

10. Lens of claim 1 wherein the lens body and wing members are made of shape retaining plastic and both the said filaments are linear tension filaments made of locally flexible and slightly resiliently stretchable plastic and cooperate to tension said frame.

11. Lens of claim 1 wherein the lens body has a generally rectangular shape and the wing members each have the shape of a segment of a circle whose chord is defined by a corresponding longer side of the inner edge forming the aperture.

12. Two piece intraocular lens for successive insertion of the two pieces through a minimum size incision into the eye for assembly therein to form the two piece lens for implantation in the eye, which comprises:

an oblong lens body having an outer edge defining two opposed longer sides and two opposed shorter sides, and a separate continous and uninterrupted ring shaped collapsible tension frame having a generally circular outer edge and an inner edge defining two opposed longer sides and two opposed shorter sides and forming an oblong aperture sized and shaped for receiving and peripherally embracing the lens body under tension, the frame including two opposed longer side oblong planar wing members defining light-masking means and two opposed shorter side collapsibly deformable linear tension filaments interconnecting correspondingly adjacent ends of the wing members to form said continuous and uninterrupted ring shaped collapsible tension frame, said filaments each being locally flexible and slightly resiliently stretchable for tensioning said frame to peripherally embrace the lens body under positive reserve tension.

13. Lens of claim 12 wherein position fixation means are provided on the frame for seating the lens in the eye.

14. Lens of claim 13 wherein the position fixation means include a haptic connected to each wing member.

15. Lens of claim 12 wherein the wing member light-masking means comprise optically opaque means.

16. Lens of claim 12 wherein the wing member light-masking means comprise optically translucent means.

17. Lens of claim 1 wherein the lens body has a generally elliptical shape and the wing members each have the shape of a convexo-concave crescent with a convex side defined by a portion of the circular outer edge of the frame and a concave side defined by a corresponding longer side of the inner edge forming the aperture.

* * * * *